US00PP24539P2

(12) United States Plant Patent

Klemm et al.

(10) Patent No.: US PP24,539 P2

(45) Date of Patent: Jun. 10, 2014

(54) POINSETTIA PLANT NAMED 'NPCW12197'

(50) Latin Name: ***Euphorbia pulcherrima* Willd. ex Klotzsch**
Varietal Denomination: NPCW12197

(71) Applicant: Klemm+Sohn GmbH & Co. KG, Stuttgart (DE)

(72) Inventors: Nils Klemm, Stuttgart (DE); Guido Von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 8 days.

(21) Appl. No.: 13/694,686

(22) Filed: Dec. 20, 2012

(51) Int. Cl.
*A01H 5/00* (2006.01)

(52) U.S. Cl.
USPC ..... Plt./307

(58) Field of Classification Search
USPC ..... Plt./307
See application file for complete search history.

*Primary Examiner* — Anne Grunberg
(74) *Attorney, Agent, or Firm* — Jondle Plant Sciences Division of Swanson & Bratschun, L.L.C.

(57) ABSTRACT

A new and distinct variety of poinsettia plant named 'NPCW12197' particularly characterized by early season flowering, large bracts and very good branching is disclosed.

1 Drawing Sheet

Genus and species: *Euphorbia pulcherrima* Willd. ex Klotzsch.

Variety denomination: 'NPCW12197'.

BACKGROUND OF THE NEW PLANT

The present invention comprises a new and distinct variety of poinsettia plant, botanically known as *Euphorbia pulcherrima* Willd. ex Klotzsch and hereinafter referred to by the variety name 'NPCW12197'. The new variety is the result of cross conducted in November and December of 2006 in Kenya, district of Nairobi, between the female parent poinsettia plant 'NPCW02044' (U.S. Plant Pat. No. 14,618) and the male poinsettia plant 'U 006' (unpatented). A single plant selection was subsequently chosen for further evaluation and asexual propagation.

'NPCW12197' was first propagated via vegetative cuttings in Stuttgart, Germany in May 2008 and has been asexually reproduced by vegetative cuttings in Stuttgart, Germany for approximately 20 generations. 'NPCW12197' has been found to retain its distinctive characteristics through successive asexual propagations via vegetative cuttings.

Plant Breeder's Rights for this variety have not been applied for. 'NPCW12197' has not been sold or made publicly available anywhere in the world more than one year prior to the filing date of this application.

SUMMARY OF THE INVENTION

The following are the most outstanding and distinguishing characteristic of this new variety when grown under normal horticultural practices in a greenhouse in Stuttgart, Germany.

1. Early season flowering;
2. Large bracts; and
3. Very good branching.

DESCRIPTION OF THE PHOTOGRAPH

This new poinsettia plant is illustrated by the accompanying photograph; the colors shown are as true as can be reasonably obtained by conventional photographic procedures. The photograph is of a whole plant about four-months-old and in full flower.

DESCRIPTION OF THE NEW VARIETY

The following detailed description sets forth the distinctive characteristics of 'NPCW12197'. The data which define these characteristics was collected from asexual reproductions carried out in Stuttgart, Germany. The plant history was taken on four month-old plants grown in 13 centimeter pots from August to December 2011 with a pinch date at week 32. The plants were grown in a greenhouse covered with glass. Color readings were taken under natural light in the greenhouse. Color references are primarily to The R.H.S. Colour Chart of The Royal Horticultural Society of London (R.H.S.) ($5^{th}$ edition 2007).

DETAILED BOTANICAL DESCRIPTION OF THE NEW PLANT

Classification:
- *Family*.—Euphorbiaceae.
- *Botanical*.—*E. pulcherrima* Willd. ex Klotzsch.
- *Common*.—Poinsettia.

Parentage:
- *Female parent*.—'NPCW02044' (U.S. Plant Pat. No. 14,618).
- *Male parent*.—'U 006' (unpatented).

Growth:
- *Time to produce a rooted cutting*.—4 weeks.
- *Blooming habit*.—Intermittent.
- *Flowering response time*.—7 weeks.
- *Keeping quality*.—Good.

Plant:
- *Form*.—V-shaped.
- *Growth habit*.—Upright.
- *Height*.—30.0 cm to 35.0 cm.
- *Width*.—30.0 cm.
- *Number of branches*.—6 to 7.
- *Average number of inflorescences per plant*.—6 to 7.

Stems:

*Color*.—Lower part: RHS 146B. Upper part: RHS 143A and RHS 59A.

*Length*.—25.0 cm to 30.0 cm.

*Internode length*.—2.0 cm to 4.0 cm.

*Diameter*.—0.5 cm to 1.0 cm.

Leaves:

*Quantity*.—8 to 15 per lateral branch.

*Arrangement*.—Alternate.

*Shape*.—Ovate.

*Apex*.—Acute.

*Base*.—Rounded.

*Margin*.—Serrate.

*Lobes*.—Quantity: Few. Lobation characteristics: Shallow.

*Texture* (*both surfaces*).—Smooth.

*Vein color*.—Upper surface: Transparent. Lower surface: RHS N139D.

*Variegation*.—Absent.

*Size*.—Length: 10.0 cm to 16.0 cm. Width: 6.0 cm to 10.0 cm.

*Color*.—Mature foliage: Upper surface: RHS 139A. Lower surface: RHS 137B. Immature foliage: Upper surface: RHS 144B. Lower surface: RHS 143C.

*Leaf petiole*.—Length: 3.0 cm to 6.0 cm. Diameter: 0.2 cm to 0.3 cm. Color: Upper surface: RHS 59A. Lower surface: RHS 59C. Texture: Smooth.

Inflorescence:

*Type and habit*.—Intermittent.

*Lastingness of inflorescence on the plant*.—3 weeks.

*Diameter*.—25.0 cm to 28.0 cm.

*Height*.—2.0 cm to 3.0 cm.

*Fragrance*.—Absent.

Bracts:

*Number of bracts per inflorescence*.—6 to 10.

*Shape*.—Ovate.

*Apex*.—Acute.

*Base*.—Rounded.

*Margin*.—Serrate.

*Lobes*.—Shallow.

*Size*.—Length: 10.0 cm to 13.0 cm. Width: 5.0 cm to 8.0 cm.

*Texture* (*both surfaces*).—Smooth.

*Venation pattern*.—Reticulate.

*Vein color*.—Upper surface: RHS 59A. Lower surface: RHS 59D.

*Bract color*.—Upper surface: RHS 46B. Lower surface: RHS 47B.

*Bract petiole*.—Length: 1.0 cm to 2.0 cm. Diameter: 0.2 cm. Color: Upper surface: RHS 59A. Lower surface: RHS 59D.

Cyme:

*Diameter*.—1.5 cm.

*Cyathia quantity*.—6 to 10 per inflorescence.

*Cyathium*.—Shape: Ovate. Diameter: 0.3 cm to 0.5 cm. Length: 0.4 cm to 0.6 cm. Color: RHS 143C.

*Peduncle*.—Color: RHS 143C. Diameter: 0.2 cm. Length: 0.1 cm to 0.2 cm. Texture: Smooth.

*Nectar cups*.—Shape: Labiate. Number: 1 per cyathium. Diameter: 0.1 cm when closed, 0.2 cm when open. Length: 0.3 cm to 0.4 cm. Color: RHS 143D when closed, RHS 14C when open.

Reproductive organs:

*Stamens*.—Quantity: 5 to 10 per cyathium. Shape: Ovate. Filaments: Length: 0.25 cm. Color: RHS 46A. Pollen: Quantity: Sparse to moderate. Color: RHS 9A to RHS 12A.

*Gynoecium*.—Present.

*Pistil quantity per cyathium*.—1.

*Pistil length*.—Approximately 0.3 cm. Stigma: Shape: Divided in 2 parts. Color: RHS 59A. Style: Length: 0.3 cm. Color: RHS 59A.

Fruit and seed set: No fruit or seed have been observed.

Disease and insect/pest resistance: Good.

COMPARISON WITH PARENTAL AND COMMERCIAL VARIETIES

'NPCW12197' differs from the female parental poinsettia plant 'NPCW02044' (U.S. Plant Pat. No. 14,618) by having medium to large elongated foliage and bracts, whereas 'NPCW02044' has smaller foliage and bracts. Additionally, 'NPCW12197' has early season flowering (7 weeks response time), whereas 'NPCW02044' has mid-season flowering (8 weeks response time).

'NPCW12197' differs from the male parental poinsettia plant 'U 006' (unpatented) by having medium sized cyathia and medium vigor, whereas 'U 006' has large cyathia and high vigor.

'NPCW12197' differs from the commercial variety 'Christmas Season' (unpatented) by having medium sized cyathia and medium vigor, whereas 'Christmas Season' has large cyathia and high vigor.

We claim:

1. A new and distinct variety of poinsettia plant named 'NPCW12197' as described and shown herein.

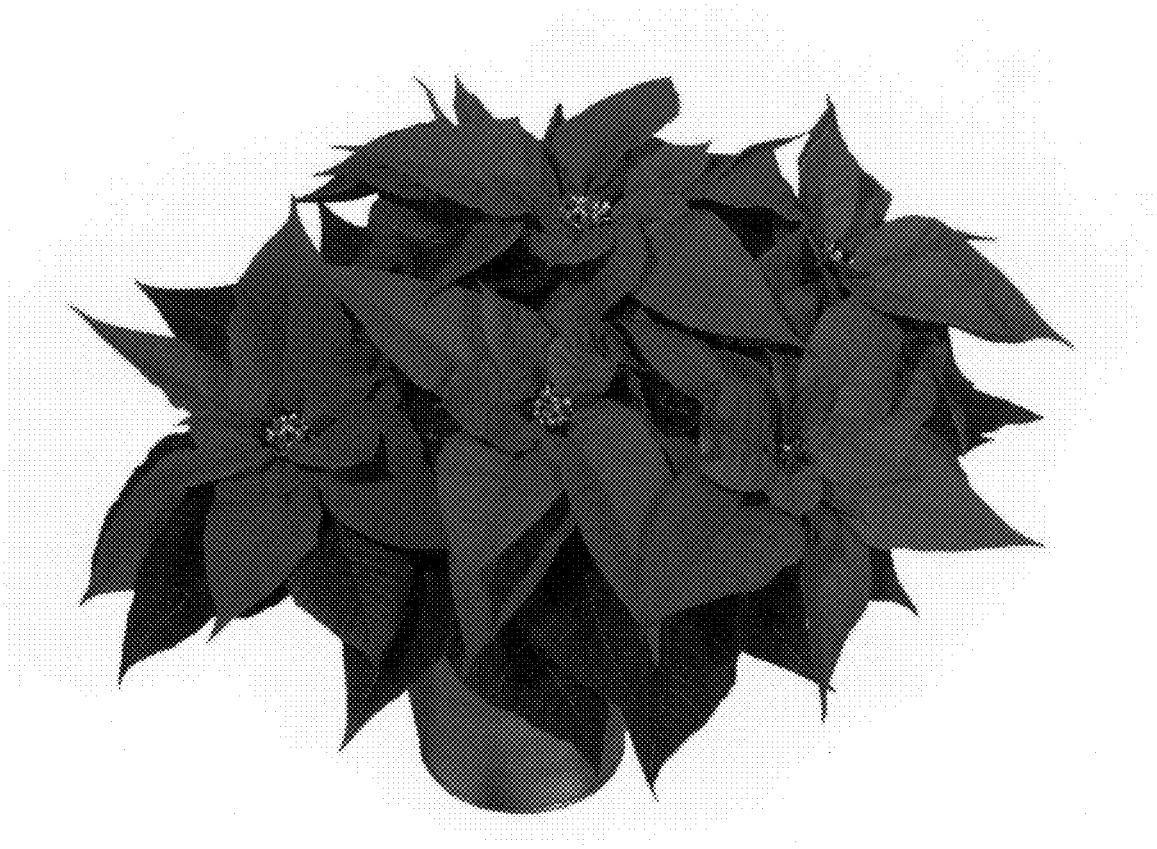

* * * * *